(12) United States Patent
Guo et al.

(10) Patent No.: US 11,920,017 B2
(45) Date of Patent: Mar. 5, 2024

(54) PREPARATION METHOD OF POLYURETHANE FOAM

(71) Applicant: NANJING TECH UNIVERSITY, Nanjing (CN)

(72) Inventors: Kai Guo, Nanjing (CN); Zheng Fang, Nanjing (CN); Chengkou Liu, Nanjing (CN); Ning Zhu, Nanjing (CN); Jingjing Meng, Nanjing (CN); Junjie Tao, Nanjing (CN); Xin Hu, Nanjing (CN); Xin Li, Nanjing (CN); Chuanhong Qiu, Nanjing (CN); Pingkai Ouyang, Nanjing (CN)

(73) Assignee: NANJING TECH UNIVERSITY, Nanjing (CN)

( * ) Notice: Subject to any disclaimer, the term of this patent is extended or adjusted under 35 U.S.C. 154(b) by 584 days.

(21) Appl. No.: 17/228,489

(22) Filed: Apr. 12, 2021

(65) Prior Publication Data
US 2021/0230390 A1     Jul. 29, 2021

Related U.S. Application Data

(63) Continuation-in-part of application No. 16/221,354, filed on Dec. 14, 2018, now abandoned.

(51) Int. Cl.
| | |
|---|---|
| *C08J 9/14* | (2006.01) |
| *C08G 18/08* | (2006.01) |
| *C08G 18/16* | (2006.01) |
| *C08G 18/66* | (2006.01) |
| *C08G 18/73* | (2006.01) |
| *C08G 18/82* | (2006.01) |

(52) U.S. Cl.
CPC ............ *C08J 9/141* (2013.01); *C08G 18/14* (2013.01); *C08G 18/168* (2013.01); *C08G 18/6685* (2013.01); *C08G 18/73* (2013.01); *C08G 18/82* (2013.01); *C08J 2203/14* (2013.01); *C08J 2205/10* (2013.01); *C08J 2375/08* (2013.01)

(58) Field of Classification Search
CPC ....................................................... C08J 9/141
See application file for complete search history.

(56) References Cited

U.S. PATENT DOCUMENTS

2013/0210951 A1*   8/2013   Hager ................... C11C 3/006
                                                      521/172

OTHER PUBLICATIONS

CN103274930 original (Year: 2013).*
CN103274930 translation (Year: 2023).*
CN101125919 original (Year: 2008).*
CN101125919 translation (Year: 2008).*
KR1631606 original (Year: 2016).*
KR1631606 translation (Year: 2016).*
Wannate PM-200 flyer (Year: 2020).*
Ji et al, ACS Sustainable Chem. Eng, 2015, 3, 1197-1204 (Year: 2015).*
Fang et al, J. Agric. Food Chem. 2019, 67, 2220-2226 (Year: 2019).*

* cited by examiner

*Primary Examiner* — Irina Krylova
(74) *Attorney, Agent, or Firm* — CBM Patent Consulting, LLC

(57) ABSTRACT

A method of a polyurethane foam includes the following steps of: (1) simultaneously pumping a mixed solution prepared from hydrogen peroxide, an organic acid, a catalyst and a stabilizer and a vegetable oil into a first microstructured reactor of a micro-channel modular reaction device for reacting to obtain a reaction solution containing epoxidized vegetable oil; (2) simultaneously pumping the reaction solution containing the epoxidized vegetable oil obtained from the step (1) and a compound of formula III into a second microstructured reactor of the micro-channel modular reaction device for reaction to obtain a vegetable oil polyol; and (3) reacting the vegetable oil polyol prepared from the step (2) with a foam stabilizer, a cyclohexylamine, an isocyanate and a foaming agent cyclopentane for foaming so as to prepare a rigid polyurethane foam.

7 Claims, 1 Drawing Sheet

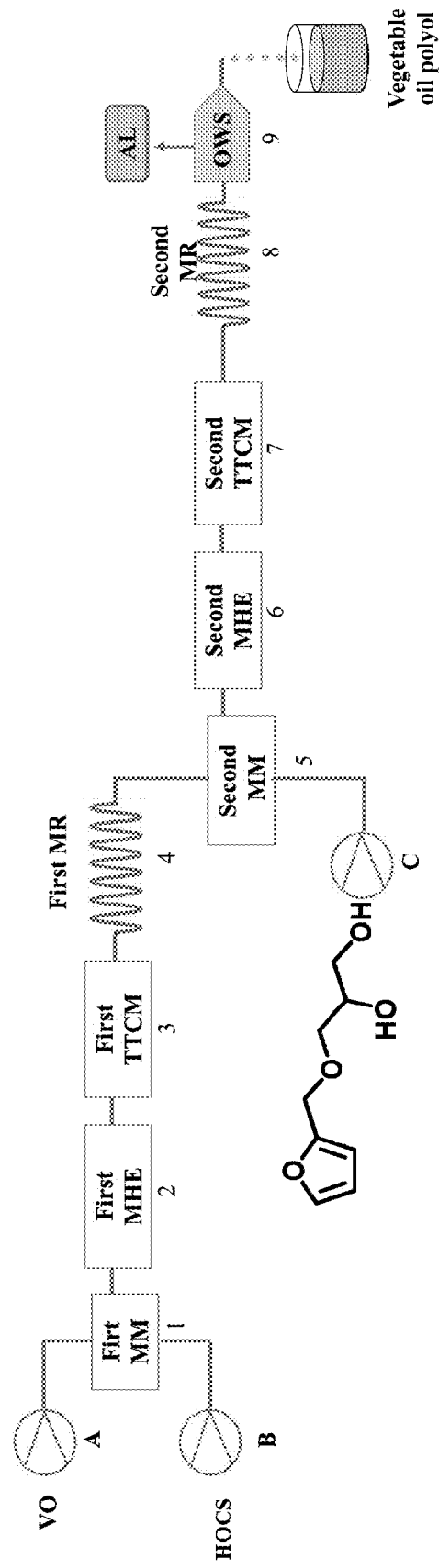
FIG.

PREPARATION METHOD OF POLYURETHANE FOAM

This application is a continuation-in-part of U.S. Ser. No. 16/221,354 filed 14 Dec. 2018 that claims priority to Chinese Patent Application Ser. No. CN201811153270.0 filed on 29 Sep. 2018.

TECHNICAL FIELD

The present invention belongs to the field of chemical materials and production technologies thereof, and particularly relates to a preparation of a polyurethane foam.

BACKGROUND

Polyurethane is prepared by reaction of isocyanate and polyol, and has a carbamate chain segment repeating unit structure, which has been widely applied to fields such as foamed plastics, surface coatings, adhesives, encapsulants and complexing agent materials. Polyurethane materials have excellent performances, wide application and diversified products, wherein a polyurethane foaming plastic has the widest application. Recently, researchers around the world are forced to prepare polyurethane with vegetable oils by the consumption of petrochemical fuel resources and the increasing concern for environmental issues.

Vegetable oil polyols are mainly used in the field of polyurethane preparation, and the prepared vegetable oil-based polyurethane materials are totally environmental friendly. Because of the hydrophobicity of fatty acid glycerides, the major components of the vegetable oils, the vegetable oil-based polyurethane materials have superior physicochemical performances, especially better hydrophobicity and thermal stability. Thereby, the vegetable oil polyols and the polyurethane materials thereof develop quickly.

The vegetable oil polyols are important renewable resources, which may react with isocyanate compounds to generate polyurethanes, and are good alternative raw materials for petroleum-based polyols. In recent years, major methods for synthesis of vegetable oil polyols include: 1) subjecting a vegetable oil and a polyol to an alcoholysis reaction to generate a polyhydroxy compound; 2) generating a polyhydroxy compound with terminal hydroxyls by oxidizing unsaturated double bonds in the vegetable oil with ozone; and 3) oxidizing the vegetable oil into epoxidized vegetable oil, then processing through hydrolysis, hydrogenation, methyl esterification or halogenation to generate a polyhydroxy compound.

Among the above methods for synthesis of the vegetable oil polyols, 1) and 3) have wider use. CN1837180A and CN101139252A relate to methods for preparing a vegetable oil polyol by a three-step reaction of alcoholysis, epoxidation and ring opening with rapeseed oil and Jatropha seed oil as the main raw materials respectively. CN10106016A relates to a method for preparing a vegetable oil polyol by a two-step reaction of epoxidation and ring opening with rubber seed oil as the main raw material. CN1907944A relates to a method for preparing a vegetable oil polyol by a two-step reaction of ring opening and alcoholysis with epoxidized rapeseed oil as the main raw material. CN101659627A relates to a method for preparing a vegetable oil polyol by simultaneously performing epoxy ring opening and ester group amidation reactions on epoxidized vegetable oil and glycolamine.

The methods for preparing the vegetable oil polyols provided by the above patents mainly based on epoxidized ring opening, all react in batch reactors, and mainly have the following defects: 1) long reaction time; 2) high energy consumption; 3) low device self-controlling level; and 4) low hydroxyl values and high viscosities of products due to the side reactions of crosslinking.

A conventional method for preparing vegetable oil polyols according to the present process is carried out in a batch mode of a reaction bottle. An epoxidized vegetable oil and most ring-opening reagents are immiscible, showing a liquid-liquid two-phase reaction, and the reaction belongs to an interface reaction. Therefore, a reaction rate is mainly controlled by mass transfer, and the reaction efficiency is low in a later stage of the reaction. It is necessary to strengthen the reaction by prolonging the time and raising the temperature, leading to more and more polyol targets as the reaction progresses slowly, which stay in the reaction system for a long time, and are prone to side reactions such as dimerization, trimerization and even tetramerization, thus making it very difficult to ensure a homogeneity of a product. Once the product is a mixture with poor homogeneity, it means that skeletons of the materials are different in sizes, and the distribution of hydroxyl groups is extremely irregular, so it is difficult to prepare a material with high homogeneity finally. In the existing design, it is very difficult to develop polyols with vegetable oils as raw materials, and there is no good solution at present. Therefore, the vegetable oil polyol and petrochemical polyol products are compounded to prepare the flexible polyurethane foam, and the advantage of relatively high homogeneity of the petrochemical polyol products is used to make up for the defects of bio-based polyols, and the bio-based polyols are dispersed into the petrochemical polyols to weaken the disadvantages of the bio-based polyols. Therefore, at this stage, there is a great need for a bio-based polyol product which can meet the requirements of preparing the polyurethane foam by using the vegetable oil polyol as the unique polyol source without adding any petrochemical polyol at all.

SUMMARY

The present invention aims to provide a totally bio-based vegetable oil polyol for the above-mentioned problems in the prior art, and the totally bio-based vegetable oil polyol is novel in structure, high in hydroxyl value and low in viscosity, and can completely replace petrochemical polyol to be applied to the field of polyurethane foam materials.

Another objective of the present invention is to provide a preparation method of the totally bio-based vegetable oil polyol. The preparation method is environment-friendly and easy to operate, and the product does not need further processing.

A final objective of the present invention is to provide a preparation method of a polyurethane foam by using the totally bio-based vegetable oil polyol as a unique polyol source.

To achieve the above objectives, technical solutions provided by the present invention are as follows:

A preparation method of a polyurethane foam includes the following steps of:

(1) simultaneously pumping a mixed solution prepared from hydrogen peroxide, an organic acid, a catalyst and a stabilizer and a vegetable oil into a first microstructured reactor of a micro-channel modular reaction device for reacting to obtain a reaction solution containing epoxidized vegetable oil;

(2) simultaneously pumping the reaction solution containing the epoxidized vegetable oil obtained from the step (1) and a compound of formula III into a second microstructured reactor of the micro-channel modular reaction device for reacting to obtain a vegetable oil polyol;

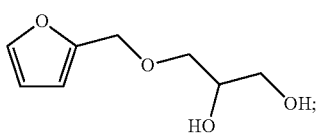

and
(3) reacting the vegetable oil polyol prepared from the step (2) with a foam stabilizer silicone oil AK-8803, a cyclohexylamine, an isocyanate and a foaming agent cyclopentane for foaming so as to prepare a rigid polyurethane foam In the preparation process, petrochemical polyol products do not need to be added additionally.

Most preferably, the preparation method of the polyurethane foam comprises the following steps of:
(1) simultaneously pumping a mixed solution of hydrogen peroxide, an organic acid, a catalyst and a stabilizer and a vegetable oil into a first micro-mixer of a micro-channel modular reaction device, uniformly mixing, then passing to a first microstructured reactor of a micro-channel modular reaction device for reacting to obtain a reaction solution containing epoxidized vegetable oil;
(2) simultaneously pumping the reaction solution containing the epoxidized vegetable oil obtained from the step (1) and a compound of formula III into a second micro-mixer of the micro-channel modular reaction device, uniformly mixing, then passing to a second microstructured reactor of the micro-channel modular reaction device for reacting to obtain a vegetable oil polyol;

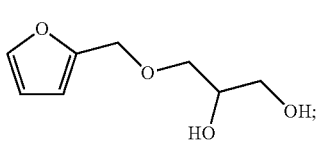

and
(3) reacting the vegetable oil polyol prepared from the step (2) with a foam stabilizer silicone oil AK-8803, a cyclohexylamine, an isocyanate and a foaming agent cyclopentane for foaming so as to prepare a rigid polyurethane foam.

In the step (1), the hydrogen peroxide has a concentration of 25-35 wt %, preferably 30 wt %. The organic acid is formic acid or acetic acid. The catalyst is sulfuric acid or phosphoric acid, preferably sulfuric acid. The stabilizer is ethylenediamine tetraacetic acid (EDTA). The vegetable oil is at least one selected from olive oil, peanut oil, rapeseed oil, cottonseed oil, soybean oil, palm oil, sesame oil, sunflower oil, linseed oil, tung oil, safflower oil, rice bran oil, corn oil and teaseed oil, preferably soybean oil or rapeseed oil, more preferably soybean oil. A molar ratio of the double bonds in the vegetable oil to the hydrogen peroxide, the organic acid, the catalyst, and the stabilizer is 1:(6 to 20):(6 to 20):(0.0.2 to 0.4):(0.006 to 0.2), preferably 1:(12 to 20:(12 to 20):(0.2 to 0.4):(0.015 to 0.1).

In the step (1), the first microstructured reactor has a reaction temperature of 60° C. to 130° C., preferably 90° C. A reaction residence time is 5 min to 10 min, preferably 8 min. A reaction pressure is normal pressure. The first microstructured reactor has a volume of 20 mL to 60 mL. The vegetable oil is pumped into the micro-channel modular reaction device at a flow rate of 0.5 mL/min to 1.0 mL/min, preferably 0.8 mL/min. The mixed solution is pumped into the micro-channel modular reaction device at a flow rate of 3.5 mL/min to 5.0 mL/min, preferably 4.7 mL/min.

In the step (2), a molar ratio of an epoxy group in the epoxidized vegetable oil to the compound of formula III is 1:(1.5 to 4.5), preferably 1:(1.5 to 2.2).

In the step (2), the second microstructured reactor has a reaction temperature of 70° C. to 100° C., preferably 85° C. A reaction residence time is 6 min to 10 min, preferably 8 min. The second microstructured reactor has a volume of 96 mL to 240 mL. The compound of formula III is pumped into the second micro-mixer at a flow rate of 12.0 mL/min to 18.0 mL/min, preferably 16.5 mL/min.

In the step (2), the reaction effluent of the second microstructured reactor is introduced into an oil-water separator, wherein an aqueous phase is removed and an oil phase product is collected, thus obtaining the vegetable oil polyol.

In the step (2), the compound of formula III is prepared by the following process:
(a) dissolving furfuryl alcohol (a compound of formula I) in a reaction solvent, dropwise adding thionyl chloride at −10° C. to 10° C., continuing stirring and reacting for 0.5 h to 2 h, adding water to quench the reaction, collecting an organic phase, and spin drying the reaction solvent to obtain colorless liquid (2-chloromethyl furan, a compound of formula II); and
(b) adding glycerol and sodium into the colorless liquid, continuing stirring and reacting for 3 h to 6 h at 30° C. to 50° C., to obtain the compound of formula III.

A synthesis route of the compound of formula III is as follows:

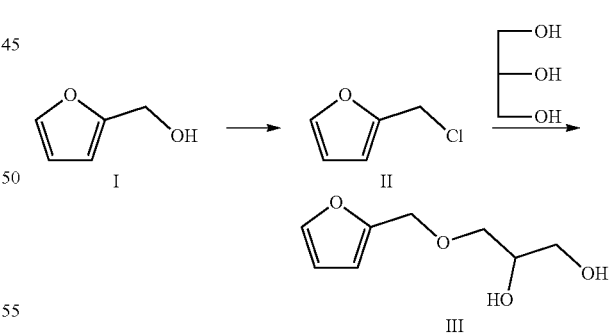

In the step (a), the reaction solvent is one or more of dichloromethane, dichloroethane, chloroform and benzene, preferably dichloromethane. A molar ratio of the furfuryl alcohol to the thionyl chloride, the glycerol, and the sodium is 1:(1.0 to 2.0):(1.0 to 2.0):(1.0 to 2.0), preferably 1:(1.0 to 1.5):(1.0 to 1.5):(1.0 to 1.5).

In the step (3), a mass ratio of the vegetable oil polyol to the foam stabilizer silicone oil AK-8803, the cyclohexylamine, the isocyanate and the foaming agent cyclopentane is 100:1.0:0.8:100:1.0.

A preparation method of the rigid polyurethane foam in the step (3) is as follows:

(1) uniformly mixing the vegetable oil polyol, the foam stabilizer AK-8803, the cyclohexylamine and the foaming agent cyclopentane according to the mass ratio, keeping the temperature at 25° C., and stirring for 10 min by using a high-speed disperser with a revolution of 1,000 r/min;

(2) keeping the isocyanate at a temperature of 25° C.; and (3) mixing and pumping the materials obtained from the step (1) and the step (2) into a mixing head of a horizontal foaming machine, mixing and stirring for 5 s, controlling a stirring speed at 5,000 r/min, continuously spraying the mixture into a mold for foaming, foaming for 120 s, and curing for 8 h at room temperature to obtain the rigid polyurethane foam.

Preferably, the compound of formula III is prepared by the following process:

(a) dissolving the furfuryl alcohol (the compound of formula I) in the reaction solvent, dropwise adding the thionyl chloride at −5° C. to 0° C., continuing stirring and reacting for 1 h to 2 h and adding water to quench the reaction, collecting the organic phase, and spin drying the reaction solvent to obtain the colorless liquid (2-chloromethyl furan, the compound of formula II); and (b) adding glycerol and sodium into the colorless liquid, continuing stirring and reacting for 4 h at 35C to 40° C., to obtain the compound of formula III.

The micro-channel modular reaction device comprises the first micro-mixer, a first microstructured heat exchanger, a first tubular temperature control module, the first microstructured reactor, the second micro-mixer, a second microstructured heat exchanger, a second tubular temperature control module and the second microstructured reactor which are sequentially connected by a pipe. The reaction materials are fed into the micro-mixer and subsequent devices via a precise pump with low pulsation level.

Preferably, the micro-channel modular reaction device further includes an oil-water separator and a receiver. A discharging outlet of the second microstructured reactor, the oil-water separator and the receiver are sequentially connected.

The first micro-mixer and the second micro-mixer are both a slit plate mixer LH25.

The first microstructured heat exchanger and the second microstructured heat exchanger are both a coaxial heat exchanger.

The first tubular temperature control module and the second tubular temperature control module are used for precisely controlling the temperatures.

The first microstructured reactor and the second microstructured reactor are each independently a meander reactor HC, a sandwich reactor HC, a fixed bed meander reactor HC or a Hastelloy micro-channel reactory.

The vegetable oil contains unsaturated carbon-carbon double bonds, which generate epoxy groups by Prileshajev epoxidation. Then hydroxyl groups are introduced into the epoxy groups by ring opening reaction. Commonly used ring-opening agents include micromolecular alcohol, alcohol amine or carboxylic acid. As for a monofunctional ring-opening agent, the hydroxyl value of a product is low, and for a polyfunctional ring-opening agent, the viscosity of a product is high viscosity and the hydroxyl value is low due to the fact that hydroxyls are adjacent to each other, a monomeric ring-opening agent performs ring-opening reaction on epoxy groups in multiple grease molecules, and newly formed hydroxyls also participate the ring opening reaction, causing the grease molecule to be polymerized. The reaction between the furfuryl alcohol and the glycerol may introduce a furan ring into the ring-opening agent and retain only one primary hydroxyl, efficiently improving the mechanical properties of the product and reducing the viscosity of the product.

The present invention employs a special polyhydroxy compound as the ring-opening agent. The ring-opening agent is a totally bio-based polyhydroxy compound prepared with furfuryl alcohol and glycerol as starting materials. The polyhydroxy compound used in the present invention have a novel structure and a proper functionality, ensuring the vegetable oil polyol prepared by ring opening reaction of the polyhydroxy compound having lower viscosity and higher hydroxyl value, and the polyurethane foam material based on the vegetable oil polyol having excellent performance. Furthermore, the catalyst selected in the present invention is used in a very small amount such that the use of the polyol will not be impacted by a trace of the remaining catalyst and the product does not need further refinement, and the process is simple.

Beneficial effects: compared with the prior art, the present invention adopts a novel environment-friendly ring-opening agent, and the obtained vegetable oil polyol is novel in structure, high in hydroxyl value, even in distribution and low in viscosity, and can completely replace traditional petrochemical polyols to prepare polyurethane foam materials. In the process of preparing the polyurethane foam, petrochemical polyol products need not be added at all. Meanwhile, the preparation method of the present invention can realize continuous operation, the preparation process is simple and easy to control, the reaction time is short, the operation is convenient, the energy consumption is low, the side reaction is less, the reaction efficiency is high, the obtained product does not need further processing and is suitable for industrial production. In the aspect of reactive mode, the present invention adopts a micro-channel modular reaction device, which can efficiently increase the reaction efficiency, inhibit the occurrence of side reactions and reduce the energy consumption.

BRIEF DESCRIPTION OF THE DRAWINGS

FIG. shows a schematic diagram of a micro-channel modular reaction device. VO=Vegetable oil; HOCS=Hydrogen peroxide Organic acid Catalyst Stabilizer; MM=micro-mixer; MHE=microstructured heat exchanger; MR=microstructured reactor; TTCM=tubular temperature control module; AL=Aqueous Layer; OWS=oil-water separator.

DETAILED DESCRIPTION

The present invention may be better understood according to the following Examples.

A vegetable oil polyol and a polyurethane foam material prepared according to the present invention are analyzed with the following methods:

(1) determining a hydroxyl value according to GB/T 12008.3-2009;

(2) determining a viscosity according to GB/T 12008.7-2010;

(3) determining an apparent density of a foam plastic according to GB/T 6343-2009;

(4) determining a compressive strength of a rigid foam plastic according to GB/T 8813-2008 with a cross section in a direction perpendicular to the foaming as a compression face, a compression rate of 5 mm/min and a measurement value at 10% deformation of a sample as a compressive strength of the material;

(5) determining an impact strength of a rigid foam plastic according to GB/T 11548-1989, wherein the impact strength is used for characterizing a toughness under high speed impact or a resistance to fracture of the materials; and (6) determining a dimensional stability of the rigid foam plastic according to GB/T 8811-2008.

As shown in FIG. 1, a micro-channel modular reaction device described in the following examples includes a first micro-mixer, a first microstructured heat exchanger, a first tubular temperature control module, a first microstructured reactor, a second micro-mixer, a second microstructured heat exchanger, a second tubular temperature control module, a second microstructured reactor, an oil-water separator and a receiver which are sequentially connected by a pipe. A feeding inlet of the first micro-mixer is connected with a first liquid storage tank (a vegetable oil storage tank) through a pump A. The feeding inlet of the first micro-mixer is connected with a second liquid storage tank (a storage tank for a mixed solution of hydrogen peroxide, organic acid, catalyst and stabilizer) through a pump B. A feeding inlet of the second micro-mixer is connected with a discharging outlet of the first micro-reactor. A feeding inlet of the second micro-mixer is connected with a third liquid storage tank (a storage tank of a compound of formula III) through a pump C.

The first micro-mixer and the second micro-mixer are both a plate mixer LH25.

The first microstructured heat exchanger and the second microstructured heat exchanger are both a coaxial heat exchanger.

The first microstructured reactor and the second microstructured reactor are each independently a meander reactor HC, a sandwich reactor HC, a fixed bed meander reactor HC or a Hastelloy micro-channel reactor.

Example 1: Preparation of Vegetable Oil Polyol (1) Preparation of Compound of Formula III 196.2 g of (2 mol) furfuryl alcohol (a compound of formula I) was dissolved in 4 L of dichloromethane, thionyl chloride (145.26 mL, 2 mol) was dropwise added into the solution at 0° C. slowly, stirring and reacting were performed at 0° C. for 1 h, and 4 L of water was added to quench the reaction. An organic layer was collected and an aqueous layer was washed for three times with dichloromethane. The organic layer was combined and the solvent was spin-dried, so as to obtain colorless liquid. 184.18 g of glycerol (2 mol) and 46 g of sodium (2 mol) were added into the liquid and stirring and reacting were continued for 4 h at 40° C. 500 mL of water was added. The organic layer was separated. The aqueous layer was extracted with toluene (250 mL*3) and the organic layer was combined. The combined organic layer was dried with anhydrous sodium sulfate and the toluene was recovered by distillation. Atmospheric distillation was carried out to obtain 292.46 g of the compound of formula III with a purity of 99.8% and a yield: 85%.

(2) Preparation of Vegetable Oil Polyol 200 g of soybean oil (containing 0.99 mol of double bonds) was taken as a component I and 1360.4 g of 30 wt % hydrogen peroxide (12 mol) was mixed with 563.63 g of formic acid (12 mol), then 20.02 g of sulfuric acid (0.2 mol, counted by $H_2SO_4$) and 4.38 g of EDTA (0.01 mol) were added as a component II, the component I and the component II were simultaneously pumped into a first micro-mixer of a micro-channel modular reaction device at feeding rates of 0.8 mL/min and mL ml/min respectively and mixed. Then the resulted mixed solution was flowed into a first microstructured reactor and reacted. The first microstructured reactor had a volume of 44 mL and a reaction residence time of 8 min. The reaction was performed at normal pressure and 90° C., thus obtaining a reaction solution containing the epoxidized vegetable oil. Next, 258 g of the compound of formula III (1.5 mol) and the reaction solution containing the epoxidized vegetable oil output by the first microstructured reactor were simultaneously pumped into a second micro-mixer of the micro-channel modular reaction device at feeding rates of 16.6 mL/min and 5.5 mL/min respectively and mixed. Then the resulted mixed solution was flowed into the second microstructured reactor and reacted. The second microstructured reactor had a volume of 176.8 mL, a reaction residence time of 8 min and a reaction temperature of 85° C. The crude reaction product was introduced into the oil-water separator to remove the aqueous phase. Then the oil phase product was collected, thus obtaining a soybean oil polyol with a hydroxyl value of 299 mg KOH/g and a viscosity of, 4736 mPa s.

Example 2: Preparation of Vegetable Oil Polyol (1) Preparation of Compound of Formula III 196.2 g of (2 mol) furfuryl alcohol (the compound of the formula I) was dissolved in 4 L of dichloromethane, thionyl chloride (217.89 mL, 3 mol) was dropwise added into the solution at 0° C. slowly, stirring and reacting were performed at 0° C. for 2 h, and 4 L of water was added to quench the reaction. An organic layer was collected and an aqueous layer was washed for three times with dichloromethane. The organic layer was combined and the solvent was spin-dried, so as to obtain colorless liquid. 184.18 g of glycerol (2 mol) and 46 g of sodium (2 mol) were added into the liquid and stirring and reacting were continued for 4 h at 40° C. 500 mL water was added. The organic layer was separated. The aqueous layer was extracted with toluene (250 mL*3) and the organic layer was combined. The combined organic layer was dried with anhydrous sodium sulfate and the toluene was recovered by distillation. Atmospheric distillation was carried out to obtain 309.67 g of of the compound of formula III with a purity 99.6% and a yield of 90%).

(2) Preparation of Vegetable Oil Polyol 200 g of soybean oil (containing 0.99 mol of double bonds) was taken as a component I and a mixture of 1700 g of 30 wt % hydrogen peroxide (15 mol) was mixed with 704.54 g of formic acid (15 mol), then 30.03 g of sulfuric acid (0.3 mol, counted by $H_2SO_4$) and 2.92 g of EDTA (0.015 mol) were added as a component II, the component I and the component II were simultaneously pumped into a first micro-mixer of a micro-channel modular reaction device at feeding rates of 0.8 mL/min and 4.7 mL/min respectively and mixed. Then the resulted mixed solution was flowed into a first microstructured reactor and reacted. The first microstructured reactor had a volume of 44 mL and a reaction residence time of 8 min. The reaction was performed at normal pressure and 90° C., thus obtaining a reaction solution containing the epoxidized vegetable oil. Next, 258 g of of the compound of formula III (1.5 mol) and the reaction solution containing the epoxidized vegetable oil output by the first microstructured reactor were simultaneously pumped into a second micro-mixer of the microchannel modular reaction device at feeding rates of 15.0 mL/min and 5.5 mL/min respectively and mixed. Then the resulted mixed solution was flowed into the second microstructured reactor and reacted. The second microstructured reactor had a volume of 164 mL, a reaction residence time of 8 min and a reaction temperature of 85° C. The crude reaction product was introduced into the oil-water separator to remove the aqueous phase. Then the oil phase product was collected, thus obtaining a soybean oil polyol with a hydroxyl value of 312 mg KOH/g and a viscosity of 4,658 mPa s.

Example 3: Preparation of Vegetable Oil Polyol (1) Preparation of Compound of Formula III 196.2 g of (2 mol) furfuryl alcohol (the compound of the formula I) was dissolved in 4 L of dichloromethane, thionyl chloride (217.89 mL, 3 mol) was dropwise added into the solution at −5° C. slowly, stirring and reacting were performed at 0° C. for 2 h, and 4 L of water was added to quench the reaction. An organic layer was collected and an aqueous layer was washed for three times with dichloromethane. The organic layer was combined and the solvent was spin-dried, so as to obtain colorless liquid. 276.27 g of glycerol (3 mol) and 69 g of sodium (3 mol) were added into the liquid and stirring and reacting were continued for 4 h at 35° C. 500 mL water was added. The organic layer was separated. The aqueous layer was extracted with toluene (250 mL*3) and the organic layer was combined. The combined organic layer was dried with anhydrous sodium sulfate and the toluene was recovered by distillation. Atmospheric distillation was carried out to obtain 302.79 g of the compound of formula III with a purity of 99.9% and a yield of 88%).

(2) Preparation of Preparation of Vegetable Oil Polyol 200 g of soybean oil (containing 0.99 mol of double bonds) was taken as a component I and 1700 g of 30 wt % hydrogen peroxide (15 mol) was mixed with 900.75 g of acetic acid (15 mol), then 30.03 g of sulfuric acid (0.3 mol, counted by $H_2SO_4$) and 2.92 g of EDTA (0.015 mol) were added as a component II, the component I and the component II were simultaneously pumped into a first micro-mixer of a micro-channel modular reaction device at feeding rates of 0.8 mL/min and 4.7 mL/min respectively and mixed. Then the resulted mixed solution was flowed into the first microstructured reactor and reacted. The first microstructured reactor had a volume of 44 mL and a reaction residence time of 8 min. The reaction was performed at normal pressure and 90° C., thus obtaining a reaction solution containing the epoxidized vegetable oil. Next, 292 g of of the compound of formula III (1.7 mol) and the reaction solution containing the epoxidized vegetable oil output by the first microstructured reactor were simultaneously pumped into a second micro-mixer of the micro-channel modular reaction device at feeding rates of 22 mL/min and 5.5 mL/min respectively and mixed. Then the resulted mixed solution was flowed into the second microstructured reactor and reacted. The second microstructured reactor had a volume of 220 mL, a reaction residence time of 8 min and a reaction temperature of 85° C. The crude reaction product was introduced into the oil-water separator to remove the aqueous phase. Then the oil phase product was collected, thus obtaining a soybean oil polyol with a hydroxyl value of 304 mg KOH/g and a viscosity of 4,895 mPa s.

Example 4: Preparation of Vegetable Oil Polyol (1) Preparation of Compound of Formula III 196.2 g of (2 mol) furfuryl alcohol (the compound of the formula I) was dissolved in 4 L of dichloroethane, thionyl chloride (217.89 mL, 3 mol) was dropwise added into the solution at −5° C. slowly, stirring and reacting were performed at 0° C. for 2 h and 4 L of water was added to quench the reaction. An organic layer was collected and an aqueous layer was washed for three times with dichloroethane. The organic layer was combined and the solvent was spin-dried, so as to obtain colorless liquid. 276.27 g of glycerol (3 mol) and 69 g of sodium (3 mol) were added into the liquid and stirring and reacting were continued for 4 h at 35° C. 500 mL water was added. The organic layer was separated. The aqueous layer was extracted with toluene (250 mL*3) and the organic layer was combined. The combined organic layer was dried with anhydrous sodium sulfate and the toluene was recovered by distillation. Atmospheric distillation was carried out to obtain 289.02 g of the compound of formula III with a purity of 99.5% and a yield of 84%.

(2) Preparation of Vegetable Oil Polyol 200 g of rapeseed oil (containing 0.785 mol of double bonds) was taken as a component I and 1700 g of 30 wt % hydrogen peroxide (15 mol) was mixed with 900.75 g of acetic acid (15 mol), then 30.03 g of sulfuric acid (0.3 mol, by $H_2SO_4$) and 2.92 g of EDTA (0.015 mol) were added as a component II, the component I and the component II were simultaneously pumped into a first micro-mixer of a micro-channel modular reaction device at feeding rates of 0.8 mL/min and 4.7 mL/min respectively and mixed. Then the resulted mixed solution was flowed into the first microstructured reactor and reacted. The first microstructured reactor had a volume of 44 mL and a reaction residence time of 8 min. The reaction was performed at normal pressure and 90° C., thus obtaining a reaction solution containing the epoxidized vegetable oil. Next, 292 g of the compound of formula III (1.7 mol) and the reaction solution containing the epoxidized vegetable oil output by the first microstructured reactor were simultaneously pumped into a second micro-mixer of the micro-channel modular reaction device at feeding rates of 19.2 mL/min and 5.5 mL/min respectively and mixed. Then the resulted mixed solution was flowed into the second microstructured reactor and reacted. The second microstructured reactor had a volume of 197.6 mL, a reaction residence time of 8 min and a reaction temperature of 85° C. The crude reaction product was introduced into the oil-water separator to remove the aqueous phase. Then the oil phase product was collected, thus obtaining a rapeseed oil polyol with a hydroxyl value of 291 mg KOH/g and a viscosity of 4,959 mPa s.

Example 5: Polyurethane Foam Prepared from Vegetable Oil Polyol

The soybean oil polyol prepared from Example 1 was reacted with a foam stabilizer AK-8803 (Maysta, Nanjing), a cyclohexylamine (Dajiang Chemical, Jiangdu), an isocyanate WANNATE® PM-200 (Wanhua Chemical, Yantai) and a cyclopentane foaming agent (Meilong Chemical, Foshan) for foaming by a one-step free foaming process, thus preparing a rigid polyurethane foam, wherein a mass ratio of the vegetable oil polyol to the foam stabilizer silicone oil AK-8803, the cyclohexylamine, the isocyanate and the foaming agent cyclopentane was 100:1.0:0.8:100:1.0, and the finally obtained polyurethane foam had an apparent density of 211 kPa, an impact strength of 0.069 kJ/m² and a dimensional stability lower than 0.8%.

Example 6

This example had the same process as Example 1, except that a molar ratio of the furfuryl alcohol to the thionyl chloride, the glycerol, and the sodium was 1:1.0:1.0:1.0. Upon detection, the resulted vegetable oil polyol had similar properties to the vegetable oil polyol prepared in Example 1.

Example 7

This example had the same process as Example 1, except that a molar ratio of the furfuryl alcohol to the thionyl chloride, the glycerol, and the sodium was 1:2.0:2.0:2.0. Upon detection, the resulted vegetable oil polyol had similar properties to the vegetable oil polyol prepared in Example 1.

Example 8

This example had the same process as Example 1, except that the catalyst was phosphoric acid, the vegetable oil was olive oil, and a molar ratio of the double bonds in the vegetable oil to the hydrogen peroxide, the organic acid, the catalyst, and the stabilizer was 1:6:6:0.02:0.006. Upon detection, the resulted vegetable oil polyol had similar properties to the vegetable oil polyol prepared in Example 1.

Example 9

This example had the same process as Example 1, except that the catalyst was phosphoric acid, the vegetable oil was peanut oil, and a molar ratio of the double bonds in the vegetable oil to the hydrogen peroxide, the organic aci, the catalyst, and the stabilizer was 1:20:20:0.4:0.2. Upon detection, the resulted vegetable oil polyol had similar properties to the vegetable oil polyol prepared in Example 1.

Example 10

This example had the same process as Example 1, except that the catalyst was phosphoric acid, and the vegetable oil was palm oil. The first microstructured reactor had a reaction temperature of 60° C., a reaction residence time of 10 min and a volume of 20 mL. A molar ratio of the epoxy groups in the epoxidized vegetable oil to the compound of formula III was 1:1.5. The second microstructured reactor had a reaction temperature of 70° C., a reaction residence time of 10 min and a volume of 96 mL. Upon detection, the resulted vegetable oil polyol had similar properties to the vegetable oil polyol prepared in Example 1.

Example 11

This example had the same process as Example 1, except that the catalyst was phosphoric acid, and the vegetable oil was sunflower oil. The first microstructured reactor had a reaction temperature of 130° C., a reaction residence time of 5 min and a volume of 60 mL. The molar ratio of the epoxy groups in the epoxidized vegetable oil to the compound of formula III was 1:4.5. The second microstructured reactor had a reaction temperature of 100° C., a reaction residence time of 10 min and a volume of 240 mL. Upon detection, the resulted vegetable oil polyol had similar properties to the vegetable oil polyol prepared in Example 1.

Comparative Example 1

A supplementary experiment was the same as Example 1, with the only difference that: the ring-opening reagent $H_2O$ of Fang et al (CN103274930) was used to replace the ring-opening reagent of instant invention. 27 g of (1.5 mol) $H_2O$ was taken. The reaction solution containing the epoxy vegetable oil output by the first microstructured reactor and the $H_2O$ were simultaneously pumped into the second micro-mixer of the micro-channel modular reaction device at the feeding rate of 2.0 mL/min and mixed. Then the resulted mixed solution was flowed into the second microstructured reactor and reacted. The second microstructured reactor had a volume of 60.0 mL, a reaction residence time of 8 min and a reaction temperature of 85° C. The feeding rate of the reaction solution containing the epoxy vegetable oil was 5.5 mL/min. The crude reaction product was introduced into the oil-water separator to remove the aqueous phase. Then the oil phase product was collected, thus obtaining a soybean oil polyol with a hydroxyl value of 403 mg KOH/g and a viscosity of 13,720 mPa s. The obtained vegetable oil polyol was not suitable for foaming due to its higher viscosity.

Comparative Example 2

A supplementary experiment was the same as Example 1, with the difference that: batch reactions were conducted in a conventional reactor. 200 g of soybean oil (containing 0.99 mol of double bonds), 1,360.4 g of 30 wt % hydrogen peroxide (12 mol), 563.63 g of formic acid (12 mol), 20.02 g of sulfuric acid (0.2 mol, counted by $H_2SO_4$) and 4.38 g of EDTA (0.01 mol) were mixed, and reacted at normal pressure and 90° C., then stirred and reacted at 600 rpm for 5 h. The obtained reaction solution containing the epoxy vegetable oil and 258 g of the compound of formula III (1.5 mol) were mixed and reacted at 85° C., stirred and reacted at 600 rpm for 8 h. The crude reaction product was introduced into the oil-water separator to remove the aqueous phase. Then the oil phase product was collected, thus obtaining a soybean oil polyol with a hydroxyl value of 161 mg KOH/g and a viscosity of 9,910 mPa s. The obtained vegetable oil polyol was not suitable for independent foaming due to its lower hydroxyl value and higher viscosity.

TABLE 1

Performance indexes of vegetable oil polyol for flexible polyurethane foam

| Performance indexes | Instant Experiments | Comparative Example 1 | Comparative Example 2 |
| --- | --- | --- | --- |
| Hydroxyl value mgKOH/g | 291-312 | 403 | 161 |
| Viscosity mPas | 4658-4959 | 13720 | 9910 |

The experiments show that the viscosity of the vegetable oil polyol is much lower in the experiments of the instant invention. However, the viscosity of the vegetable oil polyol from the two comparative experiments is too high to be suitable for foaming Therefore, only the ring-opening reagent of the instant invention being reacted in the microstructured reactor is able to produce the vegetable oil polyol for foaming with a low low viscosity, which is an unexpected result.

What is claimed is:

1. A method for preparing a rigid polyurethane foam, comprising the following steps of:

(1) simultaneously pumping a mixed solution prepared from a hydrogen peroxide, an organic acid, a catalyst, a stabilizer and a vegetable oil into a first microstructured reactor of a micro-channel modular reaction device for reacting to obtain a reaction solution containing epoxidized vegetable oil; wherein a molar ratio of double bonds in the vegetable oil to the hydrogen peroxide to the organic acid to the catalyst to the stabilizer is 1:(6 to 20):(6 to 20):(0.02 to 0.4):(0.006 to 0.2);

(2) simultaneously pumping the reaction solution containing the epoxidized vegetable oil obtained from the step (1) and a compound of formula III below into a second microstructured reactor of the micro-channel modular reaction device for reacting to obtain a vegetable oil polyol; wherein a molar ratio of an epoxy group in the epoxidized vegetable oil to the compound of formula III is 1:(1.5 to 4.5) and wherein the produced vegetable oil polyol is having hydroxyl value of 291-312 MCI KOH/g and viscosity of 4,658-4,959 mPas

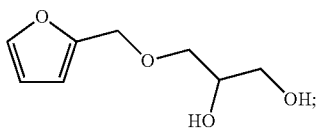

and (3) reacting the vegetable oil polyol prepared from the step (2) with a foam stabilizer silicone oil AK-8803, a cyclohexylamine, a diphenylmethane diisocyanate and a foaming agent cyclopentane for foaming so as to prepare the rigid polyurethane foam, wherein in the step (3), a mass ratio of the vegetable oil polyol to the foam stabilizer silicone oil AK-8803, the cyclohexylamine, the diphenylmethane diisocyanate and the foaming agent cyclopentane is 100:1.0:0.8:100: 1.0; and wherein the produced polyurethane foam is having impact strength of 0.069 kJ/m².

2. The method according to claim 1, wherein, in the step (1), the organic acid is formic acid or acetic acid, the catalyst is sulfuric acid or phosphoric acid, the stabilizer is ethylenediamine tetraacetic acid, the vegetable oil is at least one selected from the group consisting of olive oil, peanut oil, rapeseed oil, cottonseed oil, soybean oil, palm oil, sesame oil, sunflower oil, linseed oil, tung oil, safflower oil, rice bran oil, corn oil and teaseed oil.

3. The method according to claim 1, wherein, in the step (1), the first microstructured reactor has a reaction temperature of 60° C. to 130° C., a reaction residence time of 5 min to 10 min and a volume of 20 mL to 60 mL, the vegetable oil is pumped into the micro-channel modular reaction device at a flow rate of 0.5 mL/min to 1.0 mL/min and the mixed solution is pumped into the micro-channel modular reaction device at a flow rate of 3.5 mL/min to 5.0 mL/min.

4. The method according to claim 1, wherein, in the step (2), the second microstructured reactor has a reaction temperature of 70° C. to 100° C., a reaction residence time of 6 min to 10 min and a volume of 96 mL to 240 mL, the compound of formula III is pumped into the micro-channel modular reaction device at a flow rate of 12.0 mL/min to 18.0 mL/min.

5. The method according to claim 1, wherein the micro-channel modular reaction device comprises a first micro-mixer, a first microstructured heat exchanger, a first tubular temperature control module, the first microstructured reactor, a second micro-mixer, a second microstructured heat exchanger, a second tubular temperature control module and the second microstructured reactor which are sequentially connected by a pipe.

6. The method according to claim 1, wherein, in the step (2), the compound of formula III is prepared by the following process:

(a) dissolving furfuryl alcohol in a reaction solvent, dropwise adding thionyl chloride into the solution at −10° C. to 10° C., continuing stirring and reacting for 0.5 h to 2 h, adding water to quench the reaction, collecting an organic phase, and spin drying the reaction solvent to obtain colorless liquid; and (b) adding glycerol and sodium into the colorless liquid, continuing stirring and reacting for 3 h to 6 h at 30° C. to 50° C. to obtain the compound of formula III.

7. The method according to claim 6, wherein, in the step (a), the reaction solvent is one or more of dichloromethane, dichloroethane, chloroform and benzene, and a molar ratio of the furfuryl alcohol to the thionyl chloride, the glycerol, and the sodium is 1:(1.0 to 2.0):(1.0 to 2.0):(1.0 to 2.0).

* * * * *